US008825179B2

(12) United States Patent
Walker et al.

(10) Patent No.: US 8,825,179 B2
(45) Date of Patent: Sep. 2, 2014

(54) IMPLANTABLE MEDICAL DEVICE LEAD INCLUDING A UNIFILAR COILED CABLE (71) Applicant: Cardiac Pacemakers, Inc., St. Paul, MN (US)

(72) Inventors: Joseph Walker, Shoreview, MN (US); G. Shantanu Reddy, Minneapolis, MN (US); Devon N. Arnholt, Shoreview, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/866,791

(22) Filed: Apr. 19, 2013

(65) Prior Publication Data
US 2013/0282093 A1 Oct. 24, 2013

Related U.S. Application Data (60) Provisional application No. 61/636,204, filed on Apr. 20, 2012.

(51) Int. Cl.
*A61N 1/05* (2006.01)
*A61B 18/14* (2006.01)
(52) U.S. Cl.
CPC . *A61N 1/056* (2013.01); *A61N 1/05* (2013.01); *A61B 18/1492* (2013.01)
USPC .......................................... 607/119; 600/373
(58) Field of Classification Search
CPC ..... A61N 1/056; A61N 1/05; A61B 18/1492; A61B 5/0422
USPC .......................................... 607/119; 600/373
See application file for complete search history.

(56) References Cited

U.S. PATENT DOCUMENTS

| 3,614,692 A | 10/1971 | Rozelle et al. |
| 4,131,759 A | 12/1978 | Felkel |

(Continued)

FOREIGN PATENT DOCUMENTS

| CN | 1762510 A | 4/2006 |
| CN | 101039619 A | 9/2007 |

(Continued)

OTHER PUBLICATIONS

Gray, Robert W. et al., "Simple design changes to wires to substantially reduce MRI-induced heating at 1.5 T: implications for implanted leads", Magnetic Resonance Imaging 23 (2005) 887-891.

(Continued)

*Primary Examiner* — Christopher D Koharski
*Assistant Examiner* — Michael Carey (57) ABSTRACT A medical device lead includes a flexible body having a proximal region with a proximal end, and a distal region with a distal end. A connector is coupled to the proximal end of the flexible body of the lead to electrically and mechanically connect the lead to an implantable pulse generator. The medical device lead also includes an electrode in the distal region of the flexible body, and a cable conductor having a proximal end electrically coupled to the connector and a distal end electrically coupled to the electrode. The cable conductor consists of a single helically coiled filar including a plurality of co-radial turns and having an outer diameter of less than about 0.020 inch (0.508 mm).

20 Claims, 3 Drawing Sheets

(56) References Cited

U.S. PATENT DOCUMENTS

| | | |
|---|---|---|
| 4,135,518 A | 1/1979 | Dutcher |
| 4,404,125 A | 9/1983 | Abolins et al. |
| 4,437,474 A | 3/1984 | Peers-Trevarton |
| 4,484,586 A | 11/1984 | McMickle et al. |
| 4,493,329 A | 1/1985 | Crawford et al. |
| 4,643,203 A | 2/1987 | Labbe |
| 4,869,970 A | 9/1989 | Gulla et al. |
| 5,003,975 A | 4/1991 | Hafelfinger et al. |
| 5,056,516 A | 10/1991 | Spehr |
| 5,074,313 A | 12/1991 | Dahl et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camp et al. |
| 5,243,911 A | 9/1993 | Dow et al. |
| 5,246,014 A | 9/1993 | Williams et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Chien et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,721,600 B2 | 4/2004 | Jorgenson et al. |
| 6,721,604 B1 | 4/2004 | Robinson et al. |
| 6,813,251 B1 | 11/2004 | Garney et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,909,256 B1 | 6/2005 | Itabashi |
| 6,920,361 B2 | 7/2005 | Williams |
| 6,925,334 B1 | 8/2005 | Salys |
| 6,949,929 B2 | 9/2005 | Gray et al. |
| 6,978,185 B2 | 12/2005 | Osypka |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,239,916 B2 | 7/2007 | Thompson et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,610,101 B2 | 10/2009 | Wedan et al. |
| 7,630,761 B2 | 12/2009 | Salo et al. |
| 7,765,005 B2 | 7/2010 | Stevenson |
| 7,917,213 B2 | 3/2011 | Bulkes et al. |
| 7,953,499 B2 | 5/2011 | Knapp et al. |
| 7,986,999 B2 | 7/2011 | Wedan et al. |
| 8,103,360 B2 | 1/2012 | Foster |
| 8,145,324 B1 | 3/2012 | Stevenson et al. |
| 8,170,688 B2 | 5/2012 | Wedan et al. |
| 8,244,346 B2 | 8/2012 | Foster et al. |
| 8,255,055 B2 | 8/2012 | Ameri |
| 8,306,630 B2 | 11/2012 | Stubbs et al. |
| 8,332,050 B2 | 12/2012 | Perrey et al. |
| 8,335,572 B2 | 12/2012 | Ameri |
| 8,391,994 B2 | 3/2013 | Foster et al. |
| 8,401,671 B2 | 3/2013 | Wedan et al. |
| 8,666,508 B2 | 3/2014 | Foster et al. |
| 8,666,512 B2 | 3/2014 | Walker et al. |
| 2002/0065544 A1 | 5/2002 | Smits |
| 2002/0072769 A1 | 6/2002 | Silvian et al. |
| 2002/111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |

(56) References Cited

U.S. PATENT DOCUMENTS

| | | |
|---|---|---|
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1* | 11/2006 | Zarembo et al. ............... 607/116 |
| 2006/0271138 A1 | 11/2006 | MacDonald |
| 2006/0247747 A1 | 11/2006 | Olsen et al. |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1* | 6/2009 | Ameri ........................ 607/119 |
| 2009/0198314 A1 | 8/2009 | Foster et al. |
| 2009/0204171 A1 | 8/2009 | Ameri |
| 2009/0210022 A1 | 8/2009 | Powers |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0234929 A1 | 9/2010 | Scheuermann |
| 2010/0249892 A1 | 9/2010 | Bulkes et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2014/0067030 A1 | 3/2014 | Walker et al. |

FOREIGN PATENT DOCUMENTS

| | | | |
|---|---|---|---|
| EP | 0897997 | B1 | 2/2003 |
| EP | 1594564 | A1 | 11/2005 |
| EP | 1852810 | B1 | 11/2007 |

(56) References Cited

FOREIGN PATENT DOCUMENTS

| | | |
|---|---|---|
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03089045 A2 | 10/2003 |
| WO | WO2004073791 A1 | 9/2004 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO20090137186 A1 | 11/2009 |
| WO | WO2010078552 A1 | 7/2010 |

OTHER PUBLICATIONS

International Search Report and Written Opinion issued in PCT/US2008/085518 on Oct. 29, 2009, 15 pages.
International Search Report and Written Opinion issued in PCT/US2009/032838, mailed May 4, 2009, 14 pages.
International Search Report and Written Opinion issued in PCT/US2009/038629, mailed Jun. 29, 2009, 11 pages.
International Search Report and Written Opinion issued in PCT/US2010/024062, mailed Sep. 27, 2010.
International Search Report and Written Opinion issued in PCT/US2010/033686 on Aug. 10, 2010, 12 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2012/055673, mailed Dec. 13, 2012, 10 pages.
Invitation to Pay Additional Fees and Partial Search Report, dated Aug. 17, 2009, issued in PCT/US2008/085533, 6 pages.
Invitation to Pay Additional Fees and Partial Search Report, issued in PCT/US2010/024062, mailed May 7, 2010.
Partial International Search Report issued in PCT/US2013/013432, mailed Jul. 17, 2013, 6 pages.
Partial International Search Report issued in PCT/US2013/037432, mailed Jul. 17, 2013, 6 pages.
"High Voltage Engineering and Testing, 2nd Edition", edited by Hugh M. Ryan, Institution of Engineering and Technology, 2001, 15 pages.
Avalanche Breakdown, Wikipedia Article, captured Apr. 6, 2010, [http://en.wikipedia.org/wiki/Avalanche_breakdown].
Basso, Christophe, "SPICE Model Simulates Spark-Gap Arrestor", Electronics Design, Strategy, and News (EDN), Jul. 3, 1997, 4 pages.
Citel Inc., Data Sheet, BH Series 2 Electrode Miniature Gas Discharge Tube Surge Arrester-8mm, May 14, 2009, 2 pages.
Hayes, David L., Chapter 4, "Generator and Lead Selection" from book entitled "Cardiac Pacing and Defibrillation A Clinical Approach", John Wiley & Sons, (c) 2000 Mayo Foundation, p. 129-157.
International Search Report and Written Opinion issued in PCT/US2009/056843, mailed Dec. 29, 2009, 13 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2011/052541, dated Mar. 9, 2012, 22 pages.
International Search Report and Written Opinion issued in PCT/US2013/037432, mailed Nov. 19, 2013, 17 pages.
International Search Report and Written Opinion issued in PCT/US2013/057732, mailed Dec. 13, 2013, 11 pages.
Partial International Search Report issued in PCT/US2011/052541, mailed Dec. 6, 2011, 4 pages.
Static Spark Gap Analysis, captured Dec. 24, 2002, [http://www.richieburnett.co.uk/static.html].

* cited by examiner

IMPLANTABLE MEDICAL DEVICE LEAD INCLUDING A UNIFILAR COILED CABLE

CROSS-REFERENCE TO RELATED APPLICATION

This application claims priority under 35 U.S.C. §119 to U.S. Provisional Application No. 61/636,204, filed on Apr. 20, 2012, entitled "Implantable Medical Device Lead Including A Unifilar Coiled Cable," which is incorporated herein by reference in its entirety for all purposes.

TECHNICAL FIELD

The present disclosure relates to implantable medical devices. More particularly, the present disclosure relates to a medical device lead including an unifilar coiled cable configured to reduce electrode heating in MRI environments.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas (T). During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Disclosed herein are various embodiments of a medical device lead including a small diameter unifilar coiled cable, as well as medical device systems including such a lead.

In Example 1, a medical device lead includes a flexible body having a proximal region with a proximal end, and a distal region with a distal end. A connector is coupled to the proximal end of the flexible body of the lead to electrically and mechanically connect the lead to an implantable pulse generator. The medical device lead also includes an electrode in the distal region of the flexible body, and a cable conductor having a proximal end electrically coupled to the connector and a distal end electrically coupled to the electrode. The cable conductor consists of a single helically coiled filar including a plurality of co-radial turns and having an outer diameter of less than about 0.020 inch (0.508 mm).

In Example 2, the medical device lead according to Example 1, wherein a pitch of the helically coiled filar is about one to about two times a diameter of the filar.

In Example 3, the medical device lead according to either Example 1 or 2, wherein the pitch of the helically coiled filar varies along at least a portion of the cable conductor.

In Example 4, the medical device lead according to any of Examples 1-3, wherein a diameter of the filar is less than about 0.003 inch (0.076 mm).

In Example 5, the medical device lead according to any of Examples 1-4, and further comprising a dielectric mandrel extending through and coaxially with the helically coiled filar.

In Example 6, the medical device lead according to any of Examples 1-5, wherein the flexible body comprises a plurality of lumens, and wherein the cable conductor extends through one of the plurality of lumens.

In Example 7, a medical device lead includes a flexible body having a proximal region with a proximal end and a distal region with a distal end. A connector is coupled to the proximal end of the flexible body of the lead to electrically and mechanically connect the lead to an implantable pulse generator. A tip electrode is at the distal end of the flexible body, and one or more ring electrodes are in the distal region of the flexible body. The medical device lead further includes a coiled conductor having a proximal end electrically coupled to the connector and a distal end electrically coupled to the tip electrode, and one or more cable conductors each having a proximal end electrically coupled to the connector and a distal end electrically coupled to one of the one or more ring electrodes. Each cable conductor consists of a single helically coiled filar including a plurality of co-radial turns. An outer diameter of each of the cable conductors is less than an outer diameter of the coiled conductor.

In Example 8, the medical device lead according to Example 7, wherein the outer diameter of each of the one or more cable conductors is less than about 0.020 inch (0.508 mm).

In Example 9, the medical device lead according to either Example 7 or 8, wherein, for each of the one or more cable conductors, a pitch of the helically coiled filar is about one to about two times a diameter of the filar.

In Example 10, the medical device lead according to any of Examples 7-9, wherein the pitch of the helically coiled filar of at least one of the one or more cable conductors varies along at least a portion of the cable conductor.

In Example 11, the medical device lead according to any of Examples 7-10, wherein, for each of the one or more cable conductors, a diameter of the filar is less than about 0.003 inch (0.076 mm).

In Example 12, the medical device lead according to any of Examples 7-11, and further comprising a dielectric mandrel extending through and coaxially with each helically coiled filar.

In Example 13, the medical device lead according to any of Examples 7-12, wherein the flexible body comprises a plurality of lumens, and wherein the coiled conductor and the one or more cable conductors extend through different lumens.

In Example 14, the medical device lead according to any of Examples 7-13, wherein the tip electrode comprises a fixation helix.

In Example 15, a medical device lead includes a flexible body having a proximal region with a proximal end, and a distal region with a distal end. A connector is coupled to the proximal end of the flexible body of the lead to electrically and mechanically connect the lead to an implantable pulse generator. One or more electrodes are in the distal region of the flexible body and are configured to deliver pacing signals and/or sense electrical activity of cardiac tissue. One or more cable conductors each have a proximal end electrically coupled to the connector and a distal end electrically coupled to one of the one or more electrodes. Each cable conductor consists of a single helically coiled filar including a plurality of co-radial turns. The outer diameter of each of the one or more cable conductors is less than about 0.020 inch (0.508 mm).

In Example 16, the medical device lead according to Example 15, wherein, for each of the one or more cable conductors, a pitch of the helically coiled filar is about one to about two times a diameter of the filar.

In Example 17, the medical device lead according to either Example 15 or 16, wherein the pitch of the helically coiled filar of at least one of the one or more cable conductors varies along at least a portion of the cable conductor.

In Example 18, the medical device lead according to any of Examples 15-17, wherein, for each of the one or more cable conductors, a diameter of the filar is less than about 0.003 inch (0.076 mm).

In Example 19, the medical device lead according to any of Examples 15-18, and further comprising a dielectric mandrel extending through and coaxially with each helically coiled filar.

In Example 20, the medical device lead according to any of Examples 15-19, wherein the filar comprises an insulative coating.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
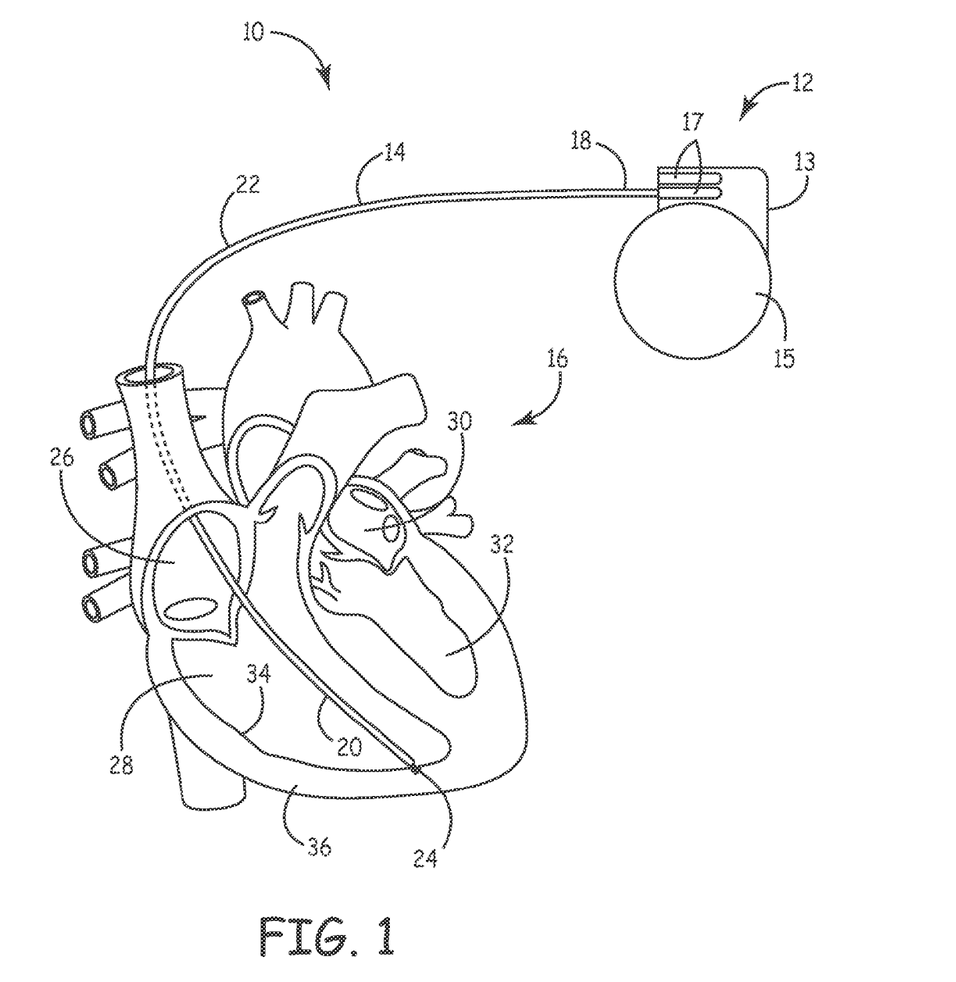
FIG. 1 is a combined cutaway of a heart and a perspective view of an implantable medical device and lead in accordance with one embodiment.

FIG. 1 is a perspective view of an implantable medical device (IMD) 10 in accordance with one embodiment. The IMD 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body, or flexible body 22, extending from the proximal region 18 to the distal region 20. The proximal region 18 is coupled to the pulse generator 12 and the distal region 20 is coupled to the heart 16. The distal region 20 includes an extendable/retractable fixation helix 24, which will be discussed in greater detail with respect to subsequent drawings, and which locates and/or secures the distal region 20 within the heart 16. In one alternative embodiment, the distal region 20 includes a plurality of tines or other structures for fixation of the lead 14 relative to the heart 20 (e.g., in a coronary vein or ventricular trabeculae). In another alternative embodiment, the lead 14 is configured as a neural lead including electrode cuffs for coupling the lead 14 to a nerve, or configured for insertion into a spinal cord.

The distal region 20 of the lead 14 has an axially compact design that accommodates a dedicated bipolar electrode configuration. The lead 14 may alternatively have other electrode configurations. As will be explained in further detail herein and shown in additional figures, one or more conductors that electrically couple the connector in the proximal region 18 of the lead 14 to one or more electrodes in the distal region 20 of the lead 14 are configured to minimize energy pickup in MRI environments to reduce heating at the electrodes.

The pulse generator 12 typically includes a connector header 13 that couples the pulse generator 12 to the lead 14. The connector header 13 typically contains one or more bores 17 that is/are able to receive a connector (not shown) that is part of a connector assembly (not shown, but see 40 in FIG. 2, discussed herein) formed near the proximal region 18 of the lead 14, wherein electrical contacts (not shown) of the connection header 13 couple with lead contacts (not shown) of the connector assembly (not shown).

The connection header 13 can be attached to a hermetically sealed enclosure 15 that contains a battery, electronic circuitry, and other components known to those skilled in the art. Electrical contacts (not shown) in the connection header 13 can be a type known to those skilled in the art that are electrically connected via feedthroughs (not shown) mounted to extend through the hermetically sealed enclosure 15 in order to electrically couple the lead 14 with pulse generator 12.

The pulse generator 12 can be implanted subcutaneously within an implantation location or pocket in the patient's chest or abdomen. In embodiments in which the lead 14 is a neural lead, the pulse generator may alternatively be implanted at the patient's back or buttocks. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from a flexible, biocompatible material suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body 22 characteristics to its intended clinical and operating environments. In various embodiments, proximal and distal ends of the lead body 22 are made from different materials selected to provide desired functionalities.

The heart 16 includes a right atrium 26, a right ventricle 28, a left atrium 30 and a left ventricle 32. The heart 16 includes an endothelial inner lining or endocardium 34 covering the myocardium 36. In some embodiments as illustrated, the fixation helix 24, located at the distal region 20 of the lead, penetrates through the endocardium 34, and is imbedded within the myocardium 36. Alternatively, the lead 14 may be configured as a passive fixation lead as discussed herein. In one embodiment, the IMD 10 includes a plurality of leads 14. For example, it may include a first lead 14 adapted to convey electrical signals between the pulse generator 12 and the right ventricle 28, and a second lead (not shown) adapted to convey electrical signals between the pulse generator 12 and the right atrium 26. Additional leads may also be employed. For example, in various embodiments, a coronary venous lead (not shown) may be utilized for stimulating a left atrium 30 and/or a left ventricle 32 of the heart 16.

In the illustrated embodiment shown in FIG. 1, the fixation helix 24 penetrates the endocardium 34 of the right ventricle 28 and is imbedded in the myocardium 36 of the heart 16. In some embodiments, the fixation helix 24 is electrically active and thus can be used to sense the electrical activity of the heart 16 or to apply a stimulating pulse to the right ventricle 28. In other embodiments, the fixation helix 24 is not electrically active. In still other embodiments, the lead 14 is fixed relative to the heart 16 using passive structures (e.g., tines, spirals, etc.).

During operation, the lead 14 can be configured to convey electrical signals between the IMD 12 and the heart 16. For example, in those embodiments in which the IMD 12 is a pacemaker, the lead 14 can be utilized to deliver electrical stimuli for pacing the heart 16. In those embodiments in which the IMD 12 is an implantable cardiac defibrillator, the lead 14 can be utilized to deliver electric shocks to the heart 16 in response to an event such as a heart attack or arrhythmia. In some embodiments, the IMD 12 includes both pacing and defibrillation capabilities.

The electrical signals are carried between the IMD 12 and electrodes at the distal region 20 by one or more conductors extending through the lead 14. The one or more conductors are electrically coupled to a connector suitable for interfacing with the IMD 12 at the proximal region 18 of the lead 14 and to the one or more electrodes at the distal region 20. According to various embodiments, the one or more conductors include coiled cables consisting of a single filar and having a small outer diameter. In some embodiments, the coiled cables are configured to deliver low voltage signals to the one or more electrodes. The coil pitch may be small (e.g., one to two times the cable filar diameter) to minimize effects of magnetic resonance imaging (MRI) scans on the functionality and operation of the lead 14.

Figure 2:
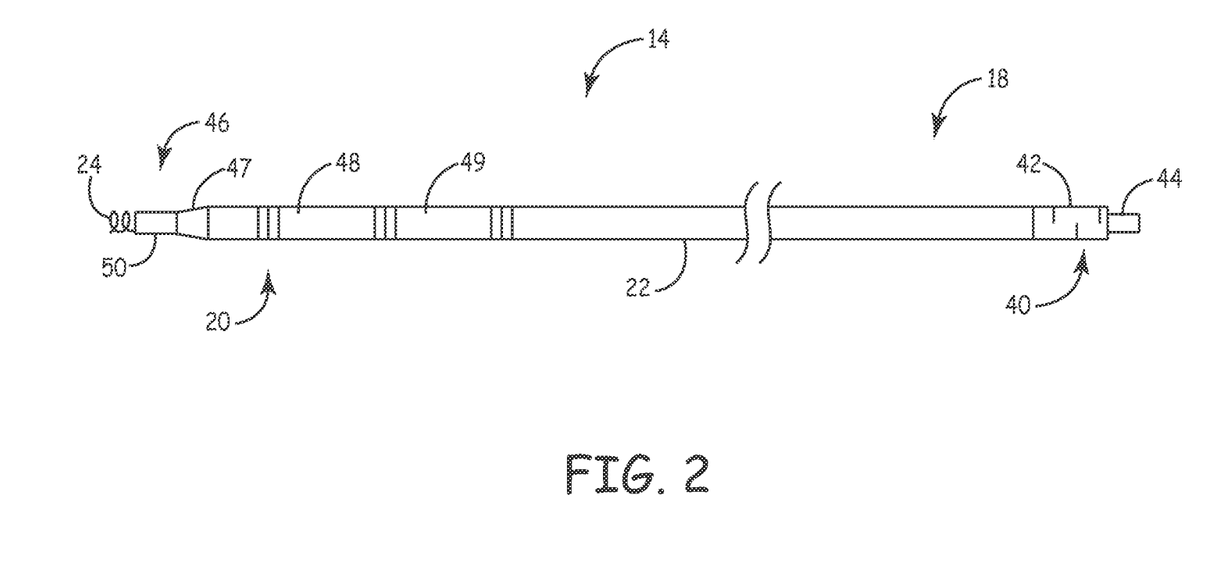
FIG. 2 is a side view of an embodiment of a lead as shown in FIG. 1.

FIG. 2 is an isometric illustration of a lead 14 according to some embodiments. A connector assembly 40 is disposed at or near the proximal region 18, or proximal end, of the lead 14. The connector assembly 40 includes a connector 42 and a terminal pin 44. The connector 42 is configured to be coupled to the lead body 22 and is configured to mechanically and electrically couple the lead 14 to the connection header 13 on the pulse generator 12 (see FIG. 1). In various embodiments, the terminal pin 44 extends proximally from the connector 42 and in some embodiments is coupled to a conductor member (not visible in this view) that extends longitudinally through the lead body 22 such that rotating the terminal pin 44 relative to the lead body 22 causes the conductor member to rotate within the lead body 22. In some embodiments, the terminal pin 44 includes an aperture (not shown) extending therethrough in order to accommodate a guide wire or an insertion stylet.

A distal assembly 46 is disposed at or near the distal region 20 or distal end of the lead 14 or lead body 22. Depending on the functional requirements of the IMD 10 (see FIG. 1) and the therapeutic needs of a patient, the distal region 20 of the lead 14 may include one or more electrodes. In the illustrated embodiment, the distal region 20 includes one or more coil electrodes 48 and 49 that can function as shocking electrodes for providing, for example, a defibrillation shock to the heart 16. In some embodiments, the coil electrodes 48 and 49 include a coating that is configured to control (i.e., promote or discourage) tissue ingrowth. In various embodiments, the lead 14 may include only a single coil electrode. In various other embodiments, the lead 14 also includes one or more low-voltage electrodes (e.g., ring electrodes), such as electrode 47, along the lead body 22 in lieu of or in addition to the coil electrodes 48, 49. When present, the low-voltage electrodes operate as relatively low-voltage, pace/sense electrodes. As will be appreciated by those skilled in the art, a wide range of electrode combinations may be incorporated into the lead 14 within the scope of the various embodiments.

The distal assembly 46 includes a housing 50, within which the fixation helix 24, or helical electrode, is at least partially disposed. As will be explained in greater detail herein, the housing 50 accommodates a mechanism that enables the fixation helix 24 to move distally and proximally relative to the housing 50, but that includes structure (not seen in this view) that limits distal travel of the fixation helix 24 (relative to the housing 50) in order to reduce or prevent over-extension of the fixation helix 24. As noted herein, the fixation helix 24 operates as an anchoring means for anchoring the distal region 20 of the lead 14 within the heart 16. In alternative embodiments, the lead 14 is fixed relative to the heart 16 using passive structures (e.g., tines, spirals, etc.).

In some embodiments, the fixation helix 24, or helical electrode, is electrically active, and is used as a low-voltage, pace/sense electrode. In some embodiments, the fixation helix 24 is made of an electrically conductive material such as ELGILOY™, MP35N™, tungsten, tantalum, iridium, platinum, titanium, palladium, stainless steel as well as alloys of these materials.

The lead 14 is one exemplary implementation of a lead in accordance with the present disclosure, and other configurations for the lead 14 are also possible. For example, while coil electrodes 48, 49 are shown adjacent to each other, the coil electrode 49 may alternatively be disposed more proximally on the lead 14. As another example, the lead 14 may include a plurality of annular electrodes along the distal region 20 for providing pacing and/or sensing signals to adjacent tissue.

Figure 3:
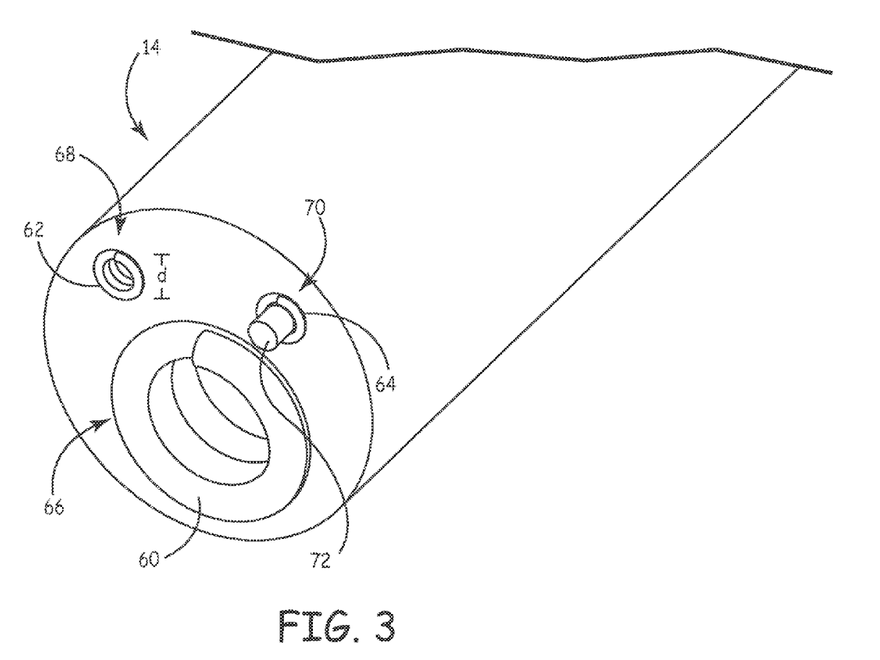
FIG. 3 is a perspective view of a portion of the lead as shown in FIG. 1 showing small diameter unifilar coiled cables extending through the lead body.

FIG. 3 is a perspective view of a portion of the lead 14 according to embodiments of the present disclosure. The lead 14 includes a coil conductor 60 and coiled cable conductors 62 and 64. In the illustrated embodiment, the lead 14 includes a lead body having a plurality of lumens 66, 68, and 70. The coil conductor 60 passes through the lumen 66, the coiled cable conductor 62 passes through the lumen 68, and the coiled cable conductor 64 passes through the lumen 70. In some embodiments, the lumens 66, 68, 70 extend substantially parallel from the connector 40 at the proximal region 18 to the distal region 20.

The coil conductor 60 is adapted for connection to the pulse generator 12 at the proximal region 18 of the lead 14. For example, the coil conductor 60 may be electrically connected to the connector 42. In the embodiment shown, the coil conductor 60 extends in parallel through the lead 14 with the coiled cable conductors 62, 64. The longitudinal axis of the coil conductor 60 is offset from the longitudinal axes of the coiled cable conductors 62, 64. In some embodiments, the coil conductor 60 is electrically coupled to one or more electrodes in the distal region 20 of the lead 14. For example, in some implementations the coil conductor 60 may be electrically coupled to the fixation helix 24 and/or the ring electrode 47. The coil conductor 60 may alternatively or additionally be connected to other electrodes. To reduce the amount of MRI-induced energy that is transmitted to the electrodes connected to the coil conductor 60, the turns of the coil conductor 60 may be tightly wound to maximize the inductance of the coil. In some embodiments, to minimize the space between adjacent turns and maximize the number of turns, the coil conductor 60 is unifilar. In other embodiments, the coil conductor 60 is multifilar.

The coiled cable conductors 62, 64 are also adapted for connection to the pulse generator 12 at the proximal region 18 of the lead 14, for example via electrical connection to the connector 42. In some embodiments, the coiled cable conductors 62, 64 are configured to carry low voltage signals between the pulse generator 12 and one or more electrodes in the distal region 20. For example, with regard to the embodiment of the lead 14 shown in FIG. 2, the coiled cable conductors 62 and/or 64 may be connected to the proximal end and/or distal end of the coil electrodes 48, 49. In this way, the coiled cable conductors 62, 64 operate to carry sensing and/or pacing signals between the pulse generator 12 and the coil electrodes 48, 49. In alternative embodiments, coiled cable conductors 62 and/or 64 may be connected to the ring electrode 47 and/or fixation helix 24.

While two coiled cable conductors 62, 64 are shown, the lead 14 may alternatively include any number of coiled cable conductors 62, 64. For example, in one alternative configuration, the lead 14 includes four cable conductors, each connected to one of the proximal or distal ends of the coil electrodes 48, 49. In another alternative configuration, the lead 14 includes a plurality of annular electrodes in the distal region, and a coiled cable conductor is connected to each of the plurality of annular electrodes.

Exposure of the lead 14 to magnetic resonance imaging (MRI) fields can result in localized heating of the electrodes at the distal region 18 due to excitation of the lead conductors (e.g., coiled cable conductors 62, 64). Conductors with high inductance (>1 μH) are more resistant to excitation in MRI fields. The inductance of the conductor is determined by its geometric properties, including whether the conductor is straight or coiled. For a coiled or wound conductor, such as the coiled cable conductors 62, 64, several parameters influence its inductance, including the coil pitch, the outer diameter of the coil 52, the cross-sectional area of the coil 52, and the number of filars comprising the coil 52. For example, in some embodiments, the coil pitch (i.e., the distance between the centers of adjacent coil turns) may be small (e.g., one to two times the cable filar diameter). The conductive coil 62 is shown having a pitch of approximately equal to the filar diameter in FIG. 3. Thus, the dimensions and characteristics of the coil 52 may be selected to minimize the effects of magnetic resonance imaging (MRI) fields on the performance and response of the lead 14.

The coiled cable conductors 62, 64 may have an outer diameter d of less than about 0.020 inch (0.508 millimeter (mm)). For example, in some exemplary implementations, the outer diameter d of the coiled cable conductors 62, 64 are in the range of about 0.008 inch to about 0.014 inch (0.203-0.356 mm). In some embodiments, the coiled cable conductors 62, 64 each consist of a single filar of conductive material (i.e., unifilar) that is helically coiled with a plurality of co-radial turns. The turns of the coiled cable conductors 62, 64 may be closely wound. For example, in some embodiments, the coiled cable conductors 62, 64 have a pitch of between about one and two times the filar diameter. The pitch may be consistent along the length of the coiled cable conductors 62, 64, or may be varied along at least a portion of the coiled cable conductors 62, 64. One exemplary approach to incorporating variable pitch sections into the coiled cable conductors 62, 64 is described in U.S. Publication 2009/0149933, entitled "Implantable Lead Having a Variable Coil Conductor Pitch," which is hereby incorporated by reference in its entirety. In some embodiments, the filar of the coiled cable conductors 62, 64 has a diameter of between about 0.0007 inch and 0.003 inch (0.018-0.076 mm). One exemplary material suitable for coiled cable conductors 62, 64 is MP35N including a silver core. Other exemplary materials suitable for coiled cable conductors 62, 64 include, but are not limited to, MPTa (MP35N with tantalum), platinum-clad Ta, platinum-clad MP35N, MP35N, and Nitinol. In some embodiments, the filar of each of the coiled cable conductors 62, 64 is insulated.

A plurality of leads including unifilar coiled cable conductors as described were exposed to an MRI environment, and the heating at the electrode attached to each of the unifilar coiled cable conductors was measured. For comparison, similar leads including bifilar and trifilar coiled cable conductors were also exposed to an MRI environment, and the associated electrodes were tested for heating. In each case, the coiled cable conductors were connected to the distal end of the distal coil electrode (e.g., coil electrode 48 in FIG. 2). The results, shown in Table 1 below, demonstrated that unifilar coiled cable conductors transmit significantly less MRI-induced energy to electrodes than corresponding multifilar configurations.

TABLE 1

| Coiled Cable Conductor Filars | Electrode Heating (° C.) |
| --- | --- |
| 1 | 1.1-1.9 |
| 2 | 2.1-2.6 |
| 3 | 4.8-5.1 |

The coiled cable conductors 62, 64 with a small outer diameter d and having a small pitch may be prone to damage during construction and use. For example, unifilar coils, such as coiled cable conductors 62, 64, may not transmit torque well, and the forces typically encountered by the lead 14 can cause the coiled cable conductors 62, 64 to experience stress concentrations in portions of the coiled cable conductors 62, 64, which can lead to premature fatigue of the coiled cable conductors 62, 64. To prevent this from occurring, the coiled cable conductors 62 and/or 64 may be formed about a flexible, non-conductive mandrel 72 that is retained after manufacturing and during use. In some embodiments, the mandrel 72 is comprised of a polymeric material, such as expanded polytetrafluoroethylene (ePTFE), layered ePTFE, polytetrafluoroethylene (PTFE), polyethylene terephthalate (PETE), ethylene/tetrafluoroethylene copolymer (ETFE), fluorinated ethylene propylene (FEP), polyether ether ketone (PEEK), polyamides, polyimides, para-aramid synthetic fibers, and polyurethane. The mandrel 72 increases the axial pull strength of the coiled cable conductors 62, 64 for later manufacturing processes and during chronic implantation. That is, the mandrel 72 improves the strength of the coiled cable conductors 62, 64 with respect to forces along the longitudinal axes of the coiled cable conductors 62, 64. This improved axial pull strength is provided by the flexible and resilient mandrel 72 substantially filling the inner diameter of the coiled cable conductors 62, 64. During manufacturing, the coiled cable conductors 62, 64 may be wrapped around the mandrel 72 in a tightly-wound configuration. In alternative embodiments, the mandrel 72 is removed from the coiled cable conductors 62, 64 after manufacturing.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead comprising:
   a flexible body formed from a polymeric material, the flexible body having a proximal region with a proximal end, a distal region with a distal end, and a plurality of lumens extending from the proximal region to the distal region, the plurality of lumens including a first lumen and a second lumen that is smaller in diameter than the first lumen;
   a connector coupled to the proximal end of the flexible body of the lead to electrically and mechanically connect the lead to an implantable pulse generator;
   a first electrode in the distal region of the flexible body;
   a second electrode in the distal region of the flexible body, the second electrode comprising a ring electrode;
   a coiled conductor extending within the first lumen from the proximal region to the distal region, the coiled conductor electrically connected to the connector and to the first electrode; and
   a cable conductor having a proximal end electrically coupled to the connector and a distal end electrically coupled to the ring electrode, the cable conductor consisting of a single helically coiled filar including a plurality of co-radial turns, the single helically coiled filar extending within the second lumen from the proximal region to the distal region, wherein the outer diameter of the coiling of each single helically coiled filar is less than about 0.020 inch (0.508 mm) and is less than the outer diameter of coiling of the coiled conductor.

2. The medical device lead of claim 1, wherein a pitch of the helically coiled filar is about one to about two times a diameter of the filar.

3. The medical device lead of claim 2, wherein the pitch of the helically coiled filar varies along at least a portion of the cable conductor.

4. The medical device lead of claim 1, wherein a diameter of the filar is less than about 0.003 inch (0.076 mm).

5. The medical device lead of claim 1, and further comprising:
   a dielectric mandrel extending through and coaxially with the helically coiled filar.

6. The medical device lead of claim 5, wherein the single helically coiled filar is wrapped around the dielectric mandrel such that the dielectric mandrel increases the axial pull strength of the cable conductor.

7. A medical device lead comprising:
   a flexible body having a proximal region with a proximal end and a distal region with a distal end, the flexible body formed from a polymeric material and having a plurality of lumens extending from the proximal region to the distal region, the plurality of lumens including a first lumen and a second lumen that is smaller in diameter than the first lumen;
   a connector coupled to the proximal end of the flexible body of the lead to electrically and mechanically connect the lead to an implantable pulse generator;
   a tip electrode at the distal end of the flexible body;
   one or more ring electrodes in the distal region of the flexible body;
   a coiled conductor having a proximal end electrically coupled to the connector and a distal end electrically coupled to the tip electrode, the coiled conductor extending within the first lumen from the proximal region to the distal region; and
   one or more cable conductors each having a proximal end electrically coupled to the connector and a distal end electrically coupled to one of the one or more ring electrodes, each cable conductor consisting of a single helically coiled filar including a plurality of co-radial turns, one of the single helically coiled filars extending within the second lumen from the proximal region to the distal region, wherein an outer diameter of the coiling of each single helically coiled filar is less than an outer diameter of the coiling of the coiled conductor.

8. The medical device lead of claim 7, wherein the outer diameter of each of the one or more cable conductors is less than about 0.020 inch (0.508 mm).

9. The medical device lead of claim 7, wherein, for each of the one or more cable conductors, a pitch of the helically coiled filar is about one to about two times a diameter of the filar.

10. The medical device lead of claim 9, wherein the pitch of the helically coiled filar of at least one of the one or more cable conductors varies along at least a portion of the cable conductor.

11. The medical device lead of claim 7, wherein, for each of the one or more cable conductors, a diameter of the filar is less than about 0.003 inch (0.076 mm).

12. The medical device lead of claim 7, and further comprising:
    a dielectric mandrel extending through and coaxially with each helically coiled filar.

13. The medical device lead of claim 12, wherein the single helically coiled filar is wrapped around the dielectric mandrel such that the dielectric mandrel increases the axial pull strength of the cable conductor.

14. The medical device lead of claim 7, wherein the tip electrode comprises a fixation helix.

15. A medical device lead comprising:
    a flexible body having a proximal region with a proximal end, and a distal region with a distal end, the flexible body formed from a polymeric material and having a plurality of lumens extending from the proximal region to the distal region, the plurality of lumens including a first lumen and a second lumen that is smaller in diameter than the first lumen;
    a connector coupled to the proximal end of the flexible body of the lead to electrically and mechanically connect the lead to an implantable pulse generator;
    at least two electrodes in the distal region of the flexible body configured to deliver pacing signals and/or sense electrical activity of cardiac tissue;
    a coiled conductor extending within the first lumen from the proximal region to the distal region, the coiled conductor having a proximal end electrically coupled to the connector and a distal end electrically coupled to one of the at least two electrodes; and
    one or more cable conductors each having a proximal end electrically coupled to the connector and a distal end electrically coupled to another one of the one or more electrodes, each cable conductor consisting of a single helically coiled filar including a plurality of co-radial turns, one of the single helically coiled filars extending within the second lumen from the proximal region to the distal region, wherein the outer diameter of the coiling of each of the single helically coiled filars is less than about 0.020 inch (0.508 mm) and is less than the outer diameter of the coiling of the coiled conductor.

16. The medical device lead of claim 15, wherein, for each of the one or more cable conductors, a pitch of the helically coiled filar is about one to about two times a diameter of the filar.

17. The medical device lead of claim 16, wherein the pitch of the helically coiled filar of at least one of the one or more cable conductors varies along at least a portion of the cable conductor.

18. The medical device lead of claim 15, wherein, for each of the one or more cable conductors, a diameter of the filar is less than about 0.003 inch (0.076 mm).

19. The medical device lead of claim 15, and further comprising:
- a dielectric mandrel extending through and coaxially with each helically coiled filar.

20. The medical device lead of claim 15, wherein the filar comprises an insulative coating.

\* \* \* \* \*